United States Patent [19]

Kothmann

[11] Patent Number: 4,682,590
[45] Date of Patent: Jul. 28, 1987

[54] METHOD OF INSERTING INTRAMEDULLARY COUPLED PIN

[76] Inventor: Kody R. Kothmann, Rte. 9, Box 73M, Lubbock, Tex. 79423

[21] Appl. No.: 795,473

[22] Filed: Nov. 5, 1985

Related U.S. Application Data

[63] Continuation-in-part of Ser. No. 595,812, Apr. 2, 1984.

[51] Int. Cl.⁴ ............................................... A61F 5/04
[52] U.S. Cl. ............................................... 128/92 YZ
[58] Field of Search .............. 128/92 R, 92 YZ, 92 Y, 128/92 YY

[56] References Cited

U.S. PATENT DOCUMENTS 2,672,861  3/1954  Jonas et al. ................... 128/92 YZ
4,467,794  8/1984  Maffei et al. ................... 128/92 YZ

*Primary Examiner*—C. Fred Rosenbaum
*Assistant Examiner*—C. W. Shedd
*Attorney, Agent, or Firm*—Wendell Coffee

[57] ABSTRACT

The intramedullary coupled pin is a rigid device for internal fixation of tubular bones in humans and animals. The device makes use of the natural marrow cavity of the bone and the musculature bridging the fracture site to cause maximum stabilization of the fractured bone. A long rod has a tip coupling on one end and a socket coupling on the other, which form the parts of the pin when cut. Each end of the rod is measured, cut and inserted into the intramedullary cavities. Then the parts of the pin are locked together at the fracture site by the coupling system of the pin. The intramedullary coupled pin is permanently implanted inside the bone because the socket system can only be unlocked by pulling the two parts of the pin directly apart.

4 Claims, 5 Drawing Figures

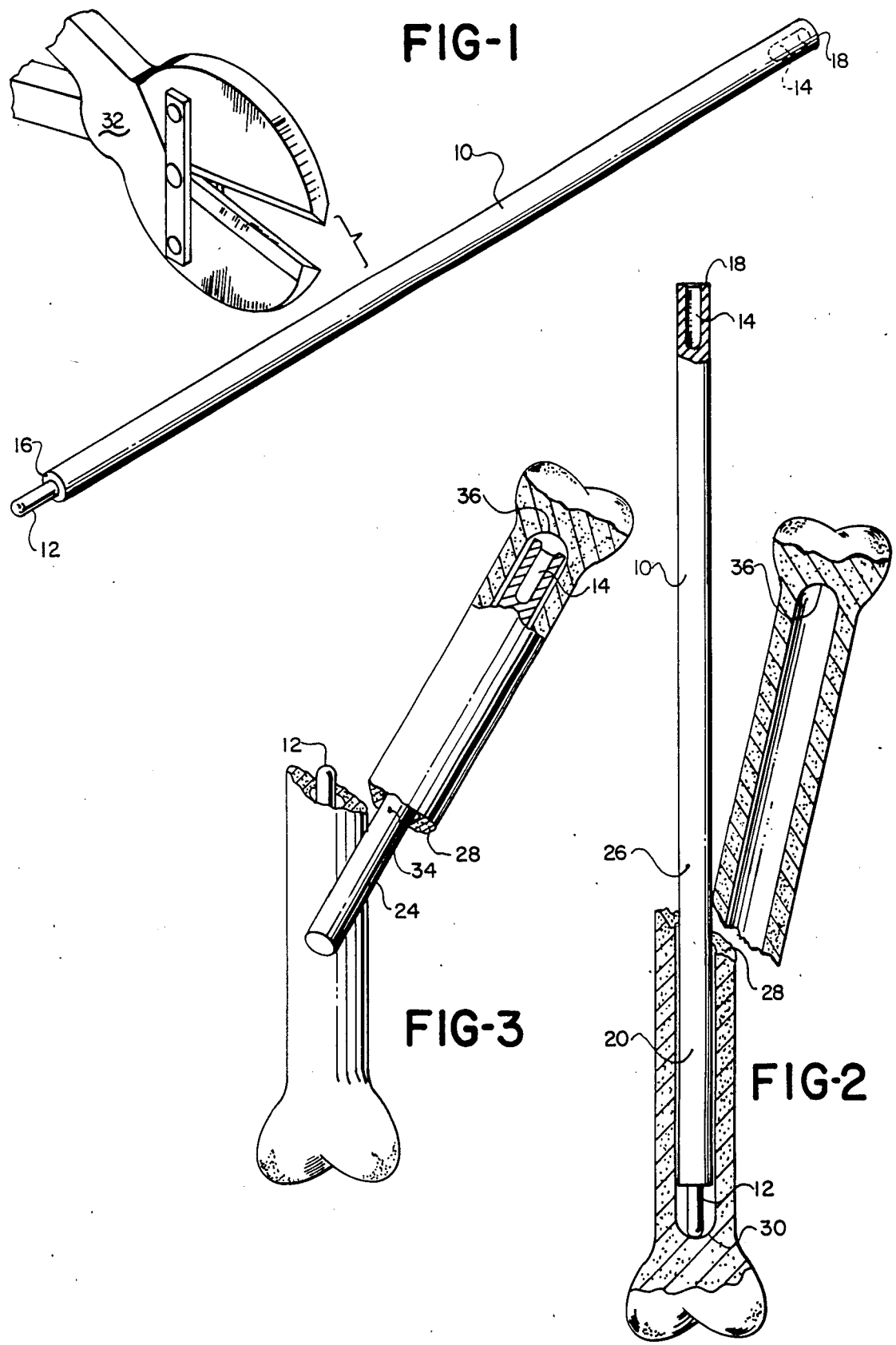

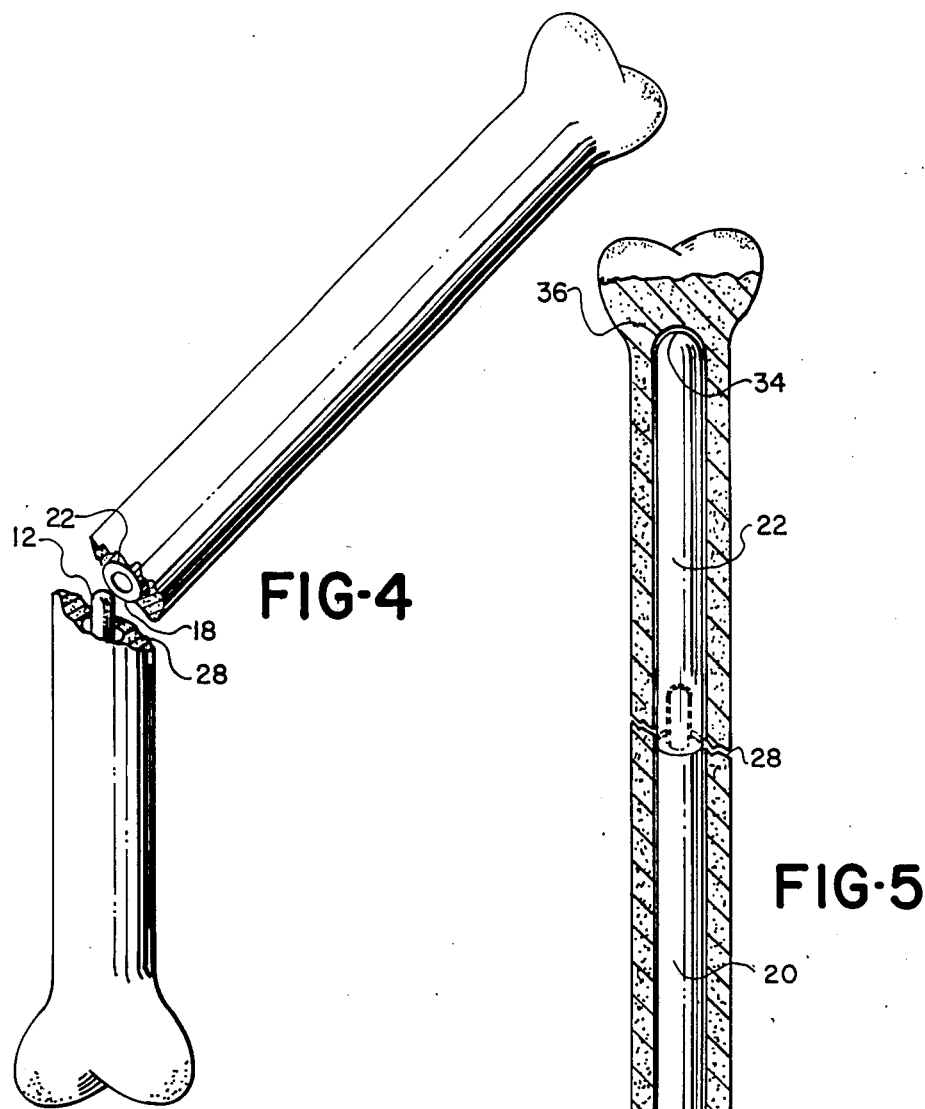

METHOD OF INSERTING INTRAMEDULLARY COUPLED PIN

CROSS REFERENCE TO RELATED APPLICATION

This is a continuation-in-part of my prior patent application Ser. No. 595,812; filed Apr. 2, 1984; entitled intramedullary pocket pin, now abandoned.

BACKGROUND OF THE INVENTION (1) Field of the Invention

This invention relates to surgery, and more particularly to a method of inserting an intramedullary coupled pin into a fractured bone.

(2) Description of the Prior Art

Immediately following a complete fracture of a tubular bone, certain physiological things occur to begin the healing process. Blood from traumatized tissue surrounding the break forms a massive clot, which later initiates the calcification process. The musculature bridging of the break loses its ability to serve the limb since there is no longer a rigid structure for insertion. Therefore, the limb loses mobility and cannot bear weight. Since muscles can only contract, the two ends of the fracture site usually overlap each other. A bone left to heal without resetting and stabilization will usually take a very long time and mend with undesirable length, straightness and strength.

The problems associated with stabilization of a tubular bone fracture are many. The surgeon must choose a method which will result in a rapidly healed bone as similar to the original as possible. The surgeon must also be aware of the joints and growth areas above and below the fracture. The surgeon should also consider a method easy to install that will yield maximum stabilization with the least possible trauma and aftercare to the patient.

The following U.S. Patents were cited by the Examiner in the prosecution of the parent application:

| Inventor | Date Filed | Issue Date | U.S. Pat. No. |
| --- | --- | --- | --- |
| Miner Et Al | Nov 13, 1929 | Oct 9, 1934 | 1,976,264 |
| Jonas Et Al | Dec 30, 1952 | Mar 23, 1954 | 2,672,861 |
| Deliso | Jul 20, 1956 | Dec 2, 1958 | 2,862,745 |
| Deliso | Jul 20, 1956 | Jan 20, 1959 | 2,869,907 |
| Jonas Et Al | Mar 19, 1959 | May 23, 1961 | 2,985,168 |
| Hollaender | Sep 29, 1958 | Sep 19, 1961 | 3,000,656 |
| Petri | Mar 10, 1971 | Dec 26, 1972 | 3,707,303 |
| Maffei Et Al | May 19, 1976 | Apr 12, 1977 | 4,016,874 |
| Maffei Et Al | Feb 8, 1982 | Aug 28, 1984 | 4,467,794 |

As may be seen, the prior workers in the treatment of a complete fracture of a tubular bone, have recognized that an intramedullary pin has certain desirable qualities. The two JONAS patents utilize a spring bias pin in which different metals for the spring and the pin often lead to complications and undesirable results in commercial practice.

The two MAFFEI ET AL patents concern pins which are anchored to the inside of the tubular bone with tapper threaded pins and then are jointed together.

The other five patents appear to be completely unrelated; however, Applicant believes a reasonable Examiner would consider any art cited by another Examiner to be of interest and pertinent to the examination of this application.

SUMMARY OF THE INVENTION (1) New and Different Function

The intramedullary coupled pin of this invention has the primary purpose of facilitating and improving the mending of the bone fractures. The pin is constructed of biocompatible rigid material, preferably stainless steel rod having a predetermined diameter, and can be used in bone fractures containing a marrow cavity proximal and distal to the fracture site. The procedure used with the intramedullary coupled pin incorporates the muscle tension bridging the fracture and the existing natural marrow cavity to cause maximum stabilization and realignment of the bone. This invention is intended to eliminate such problems as expensive orthopedic tools, unnecessary external wounds, poor bone stabilization, joint stiffness below or above the fracture, and intensive tedious aftercare of the healing bone fracture.

The preferred embodiment begins with a single rod having a diameter that will fit snugly within the marrow cavity and longer than the length of the marrow cavity between the cancellous bone at each end of the marrow cavity. One end of the single rod will have a tip coupling. The other end of the single rod will have a socket coupling of a diameter and length to mate snugly with the tip coupling.

The rod is measured and cut with regular metal working tools so that the cut end of the rod will be at the end of the marrow cavity. Then, this portion of the rod is inserted into the marrow cavity of the bone with the tip coupling at the fracture site.

Then the remaining portion of the rod is inserted into the marrow cavity with the socket coupling against the cancellous bone and the rod measured to the proper length. Then the rod is removed from the marrow cavity, cut, and reversed so that the socket coupling is also at the fracture site. The bone is then extended so that the tip mates into the socket and the muscle tension pulls the couplings of two portions of the rod together forming a snug fit with the portions of the fractured bone in the approximate location of the bone before fracture.

(2) Objects of this Invention

An object of this invention is to set completely fractured tubular bones.

Other objects are to achieve the above with a method that is rapid, versatile, ecologically compatible, energy conserving, efficient, and inexpensive, and does not require highly skilled people to connect, adjust, operate, and maintain complex apparatus.

The specific nature of the invention, as well as other objects, uses, and advantages thereof, will clearly appear from the following description and from the accompanying drawing, the different views of which are not scale drawings.

BRIEF DESCRIPTION OF THE DRAWINGS:

FIG. 1 is an perspective view of the rod in its original form with cutting instrument shown.

FIG. 2 is a schematic representation of a fractured bone with the rod being measured.

FIG. 3 is a schematic representation of the rod with the tip pin part within one portion of the fractured bone, and the remainder of the rod being measured and cut.

FIG. 4 is a schematic representation with the two parts of the rod within the broken bone with the tip coupling and the socket coupling each at the fracture site before mating.

FIG. 5 is a schematic representation with the intramedullary pin joined with the tip within the socket and the bone immobilized.

DESCRIPTION OF THE PREFERRED EMBODIMENT:

Referring to the drawing, rod 10 may be seen. The rod is biocompatible and rigid. The diameter is selected to snugly fit within the marrow cavity of a fractured tubular bone. In practice, a plurality of rods would be prepared, each having a different diameter. The rods would be longer than the expected need. Therefore, the surgeon, at the beginning of the procedure, would select that rod which had a diameter which would fit snugly into the marrow cavity. Stainless steel is the preferred material for the rod 10.

Tip coupling 12 is on one end of the rod 10 and socket coupling 14 upon the other end. Tip coupling 12 is a cylindrical coaxial tip which has a tip diameter of approximately ½ the diameter of the original rod 10. The tip length will be approximately 1½ the diameter of the original rod. The distal end of the tip coupling 12 will be slightly rounded.

The socket coupling 14 will be a cylindrical bore of only slightly larger diameter than the tip so that the tip forms as tight a fit as possible with the parts still fitting smoothly and easily upon insertion. The bore will be slightly deeper than the tip length so that upon assembly, tip shoulder 16 of the tip coupling bears against socket shoulder 18. The socket shoulder is slightly beveled inward so that the outer edge forms a smooth seam with the edge of the tip shoulder 16. The rod 10 will form two pin parts; tip pin part 20 and socket pin part 22. The rod 10 from which the two pin parts are cut will be made longer than any bone in which it is expected to be used so that there will be center waste part 24.

The surgeon chooses the pin with the proper diameter to fit snugly within the marrow cavity of the fractured bone and sterilizes the pin. Next, the surgeon measures the pin from the tip coupling 12 to the tip rod cut point 26. This may be done in any number of ways. The preferred method is that the tip coupling 12 of the rod 10 is inserted into the fractured bone until the tip coupling 12 seated against cancellous bone 30 at the end of the marrow socket and the rod marked at the tip rod cut point 26. The rod is then cut by metal cutting means such as bolt cutter 32.

Regardless of how the length from the cancellous bone 30 to fracture site 28 is measured and the tip rod cut point 26 determined, the rod is cut. Once cut, this part of the rod 10 is then designated as the tip pin part 20 of the final pin. Once cut, then this tip pin point is inserted into the bone with the tip rod cut point 26 seated against the cancellous bone 30.

After this is done, the socket rod cut point 34 is determined. This is by a measurement process as described for the tip rod cut point 26. The preferred method for determining the socket rod cut point 34 is to insert the socket coupling 14 into the marrow cavity of the bone until the cavity socket 14 is against cancellous bone 36. Then the rod is removed and cut at the socket rod cut point 34. The pin part 22 is then reinserted into the fractured bone with the socket rod cut point 34 firmly against the cancellous bone 36.

Then, the two parts of the bone are aligned and the tip at coupling 12 inserted into the socket at coupling 14 so that the fractured bone is set, as seen in FIG. 5. As soon as the bones are aligned, the surgeon allows the tension of the musculature to pull the tip into the socket. Once this is done, it may be seen that the two pin parts 20 and 22 are aligned, thus aligning the two parts of the fractured bone. Also, it may be seen that the two pin parts then form one single unitary pin which is strong and rigid. Once joined, the coupling can only be disconnected by moving the bone parts axially away from one another against the muscle tension.

The unitary pin is cut from the single rod 10 so there is no possibility of electrolysis caused by dissimilar metals.

The coupling system is held in place because the ends 26 and 34 of the pin will not penetrate into the cancellous bone 30 or 36, as shown in FIG. 5. The musculature bridging the pinned fracture also tends to pull the bones back to their original position.

It is clear that the most important part of the entire procedure is the measurement and cutting. The surgeon may choose his own method of measurement but what seems to work best is to place the rods as far as possible into the respective marrow cavity with a portion of the rods remaining outside the marrow cavity. The portion of the rods remaining outside of the marrow cavity are removed, cut and the rods reinserted with the coupling at the fracture site. The rod with the tip should be cut so that the length of the tip will extend beyond the marrow cavity as shown in FIG. 3. On any fracture, especially spiral, the measurement taken must be from the area on the bones that will be in apposition with each other when the bone is set and the pin is in place.

The surgeon may choose to cut the pin parts slightly long and drive the cut ends 26 and 34 into the spongy cancellous bone for a perfect fit. Cutting the rods slightly long is preferable to cutting the pin parts short.

Finally, the two rods or pin parts become the intramedullary coupling pin when the rounded tip of coupling 12 slides into the beveled bore of coupling 14. The lower fracture in the limb is manipulated until the coupling locks. When this happens, the two fractured ends will be in direct apposition and the bone should be as rigid as an unbroken bone (FIG. 5). The forces upon the bone surrounding the pin will keep the coupling immobile. But most important, the pin and the muscle will keep the bone immobile.

The embodiment shown and described above is only exemplary. I do not claim to have invented all the parts, elements or steps described. Various modifications can be made in the construction, material, arrangement, and operation, and still be within the scope of my invention.

The limits of the invention and the bounds of the patent protection are measured by and defined in the following claims. The restrictive description and drawing of the specific examples above do not point out what an infringement of this patent would be, but are to enable on skilled in the art to make and use the invention.

As an aid to correlating the terms of the claims to the exemplary drawing, the following catalog of elements and steps is provided:

| 10 | Rod | 24 | Waste Part |
|----|-----|----|------------|
| 12 | Tip Coupling | 26 | Tip Rod Cut Point |
| 14 | Socket Coupling | 28 | Fracture Site |
| 16 | Tip Shoulder | 30 | Cancellous Bone |
| 18 | Socket Shoulder | 32 | Bolt Cutter |
| 20 | Tip Pin Part | 34 | Socket Rod Cut Point |

| | -continued | | |
|---|---|---|---|
| 22 | Socket Pin Part | 36 | Cancellous Bone |

I claim:

1. The method of immobilizing a fractured tubular bone having a marrow cavity using:

two rods joined at a coupling which locks the rods into a pin which can only be unlocked by pulling the rods axially apart, said pin having two ends, one end on each rod;

COMPRISING THE STEPS OF:

choosing a pin diameter which will fit snugly into the marrow cavity, cutting the end from each rod so with each rod inserted into the marrow cavity with the cut end against the cancellous bone that the coupling of each rod is at the fracture, inserting each rod into the fractured bone, and joining the rods at the coupling to form the pin.

2. The invention as defined in claim 1 further comprising:

measuring the amount of each rod to be cut off by inserting each rod into the marrow cavity of the portion of the bone in which it will be permanently placed, then measuring the distance each rod projects from the fracture, then cutting the measured distance of each rod from the end of that rod.

3. The method of immobilizing a fractured tubular bone having a marrow cavity with cancellous bone at each and with muscle connecting the two fractured parts using:

a pin in the marrow cavity having a tip and socket coupling at the fracture;

COMPRISING THE STEPS OF:

preparing a rod having a diameter which will fit snugly into the marrow cavity, the rod having a tip coupling on one end and a socket coupling on the other end, measuring the tip coupling to tip rod cut point to match the fracture site to cancellous bone distance of one part of the fractured bone, cutting the rod at the tip rod cut point to form a tip pin part, inserting the tip pin part in the matching part of the fractured bone with the tip coupling at the fracture and the cut point at the cancellous bone, measuring the socket coupling to the socket rod cut point to match the fracture site to cancellous bone of the other part of the fractured bone, cutting the rod at the socket rod cut point to form a socket pin part, inserting the socket pin part in the matching part of the fractured bone with the socket coupling at the fracture and the cut point at the cancellous bone, aligning the parts of the fracture bone, and allowing the muscle tension to pull the tip coupling into engagement with the socket coupling.

4. The invention as defined in claim 3 wherein:

the measuring of the tip coupling to the tip rod cut point is by inserting the tip coupling into the marrow cavity until the tip coupling is against the cancellous bone, and the measuring of the socket coupling to the socket rod cut point is by inserting the socket coupling into the marrow cavity until the socket coupling is against the cancellous bone.

* * * * *